United States Patent
Mao et al.

(10) Patent No.: US 8,352,038 B2
(45) Date of Patent: Jan. 8, 2013

(54) MEDICAL DEVICE FUNCTION CONFIGURATION POST-MANUFACTURING

(75) Inventors: Bor-Jiin Mao, Roseville, MN (US); Mark L. Haerle, Bloomington, MN (US); Kathleen U. Crandall, Champlin, MN (US); Patricia K Fuher, Brooklyn Park, MN (US); Michael Lee Graham, St. Michael, MN (US)

(73) Assignee: Medtronic, Inc., Minneapolis, MN (US)

( * ) Notice: Subject to any disclaimer, the term of this patent is extended or adjusted under 35 U.S.C. 154(b) by 1149 days.

(21) Appl. No.: 11/865,294

(22) Filed: Oct. 1, 2007

(65) Prior Publication Data
US 2009/0088820 A1   Apr. 2, 2009

(51) Int. Cl.
*A61N 1/00* (2006.01)
(52) U.S. Cl. .......................................... 607/59
(58) Field of Classification Search ............... 607/5, 30, 607/31, 59
See application file for complete search history.

(56) References Cited

U.S. PATENT DOCUMENTS

| | | |
|---|---|---|
| 5,354,319 A | 10/1994 | Wyborney et al. |
| 5,456,692 A | 10/1995 | Smith et al. |
| 5,725,559 A | 3/1998 | Alt et al. |
| 5,800,473 A | 9/1998 | Faisandier |
| 6,442,432 B2 | 8/2002 | Lee |
| 6,482,154 B1 | 11/2002 | Haubrich et al. |
| 6,497,655 B1 | 12/2002 | Lindberg et al. |
| 6,880,085 B1 | 4/2005 | Balczewski et al. |
| 7,060,031 B2 | 6/2006 | Webb et al. |
| 7,181,505 B2 | 2/2007 | Haller et al. |
| 2001/0051787 A1 | 12/2001 | Haller et al. |
| 2003/0055406 A1 | 3/2003 | Lebel et al. |
| 2003/0144711 A1 | 7/2003 | Pless et al. |
| 2005/0107839 A1 | 5/2005 | Sanders |
| 2005/0283198 A1 | 12/2005 | Haubrich et al. |
| 2007/0100397 A1 | 5/2007 | Seeberger et al. |
| 2007/0136098 A1 | 6/2007 | Smythe et al. |

OTHER PUBLICATIONS

PCT Search Report for International Application No. PCT/US2008/078314.

*Primary Examiner* — Eric D. Bertram
*Assistant Examiner* — Elizabeth K So (57) ABSTRACT

A medical device system and method configure a medical device according to a configuration definition. The configuration definition includes an allowable status and a function status for each of a number of medical device functions. The medical device configuration is updated automatically in response to being interrogated by a programmer configured to update the device configuration. The device configuration is updated by updating the function status for at least one of the medical device functions in response to the allowable status for the medical device function.

19 Claims, 6 Drawing Sheets

MEDICAL DEVICE FUNCTION CONFIGURATION POST-MANUFACTURING

TECHNICAL FIELD

The invention relates generally to medical devices and, in particular, to systems and methods for configuring medical device functionality after manufacturing.

BACKGROUND

Medical devices are often commercially released for use with patients while new features or functions of the medical device are still under investigation due to the continuum of medical research. New functions may become available based on ongoing research or regulatory agency approval after the medical device is already in use. Since new functions may be beneficial to patients already having an existing model of the medical device, it is desirable to distribute the new functionality to these patients in a time-efficient, cost-effective manner. Manufacture and distribution of newly manufactured models including new functions is costly and timely, and may pose risk or inconvenience to the patient if the device is an implantable medical device that needs to be explanted and replaced with the new model.

Furthermore, patients may be indicated for different functions of a medical device based on their diagnostic or therapeutic needs. For example one patient may be indicated for a full function implantable cardioverter defibrillator (ICD) while another patient may only need ambulatory monitoring for arrhythmias for diagnostic purposes to determine the patient's risk for arrhythmias or need for arrhythmia therapies. The later patient would not require a more costly, full-function ICD but could be well-served by a less-costly implantable diagnostic device having limited functionality. However, manufacturing and distributing many different models of medical devices to suit varying medical needs can be costly and complicated. Furthermore, if the later patient in the above example is ultimately diagnosed as needing a full function ICD, explantation of the lower cost, diagnostic device and implantation of the full function ICD would be required, resulting in two different devices and implantation procedures being required for the same patient. For a number of reasons, therefore, there is a need to allow medical device functionality to be reconfigured post-manufacturing.

DETAILED DESCRIPTION

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Methods described in conjunction with flow charts and other diagrams presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software or firmware modules, which may be executed by themselves or in combination with other software or firmware.

Figure 1:
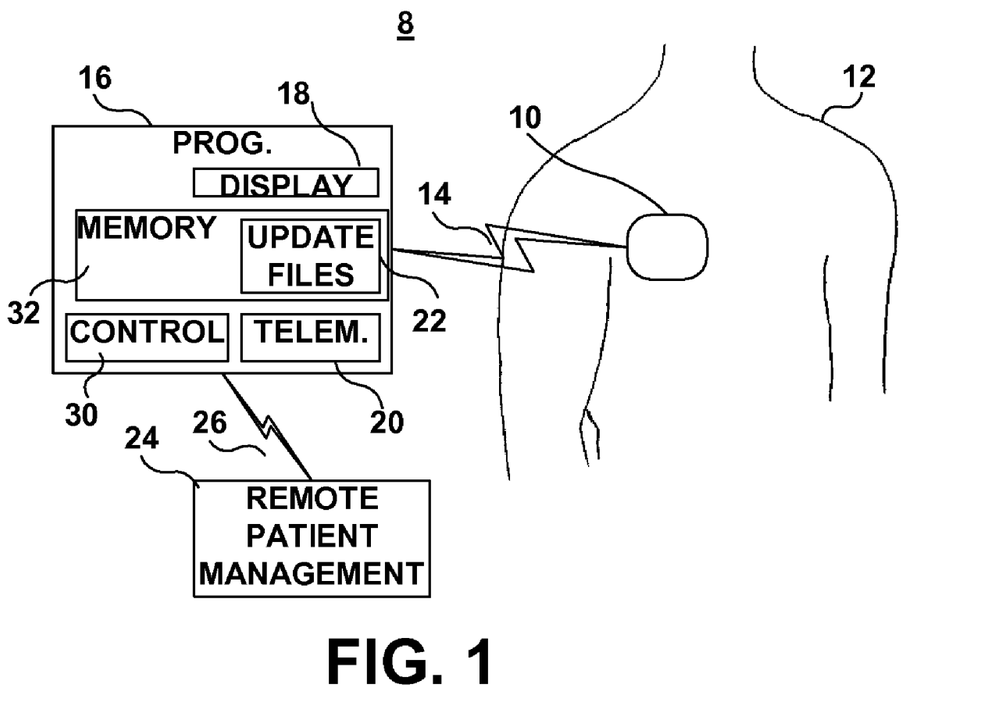
FIG. 1 is a schematic diagram of one medical device system in which the present invention may be embodied.

FIG. 1 is a schematic diagram of one medical device system 8 in which the present invention may be embodied. The medical device system 8 includes an implantable medical device (IMD) 10, shown implanted in a patient 12, and a programmer 16 configured for bidirectional communication with IMD 10 via a telemetry link 14. IMD 10 may be any programmable therapy delivery or monitoring device such as a pacemaker, cardioverter defibrillator, cardiac monitoring device, drug delivery device, neurostimulator, blood glucose monitor, or the like. Programmer 16 is used to program operating parameters used to control functions of IMD 10 relating to monitoring a patient and/or delivering patient therapies. As will be described herein, programmer 16 is also used to update the functional configuration of IMD 10.

Programmer 16 includes a display 18, telemetry circuitry 20, a control module 30 and associated memory 32 for storing update files 22 used for updating a configuration of IMD 10 as will be described herein. Control module 30 controls programmer functions, such as telemetry communications, programming of IMD 10, and display of programming and IMD data, according to software implemented in programmer 16 and stored in memory 32. Telemetry circuitry 20 is used to establish a communication link 14 with IMD 10 and control the transmission of data between IMD 10 and programmer 16. Display 18 is used for presenting programmable operating parameters of IMD 10, selectable values for the programmable operating parameters, and physiological data or device diagnostic data retrieved from IMD 10 as well as other messages, alerts or user-entered information for viewing by a user.

IMD 10 is configured at the time of device manufacture to a first device configuration. As used herein, the term "device configuration" refers to a particular combination of enabled and disabled device functions. Enabled device functions are those that are enabled to be available to a user and operate according to programmable (and/or non-programmable) operating parameters during IMD operation. Disabled device functions are those functions that are not available to a user and are prevented from operating during IMD operation, regardless of user-programmed operating parameters.

IMD 10 may be manufactured to be capable of performing one or more functions that are initially disabled in a first device configuration. In one example embodiment, IMD 10 is an implantable cardioverter defibrillator (ICD). In this embodiment, IMD 10 may capable of performing a number of arrhythmia detection functions and a number of arrhythmia therapy delivery functions. The arrhythmia detection functions may include functions performed for detecting varying severities of arrhythmia episodes such as less serious atrial arrhythmias and more serious ventricular tachycardias and fibrillation. A first configuration of IMD 10 set at the time of device manufacture might include enabling all arrhythmia detection functions and disabling all arrhythmia therapy delivery functions (perhaps with the exception of defibrillation therapy for treating ventricular fibrillation, the most serious form of detected arrhythmias). The disabled therapy delivery functions will not be available to a user. The enabled arrhythmia detection functions will operate under the control of user-programmable operating parameters (and any non-programmable operating parameters). The programmable operating parameters may include turning an enabled function "on" or "off". As such, a clinician may have the option of turning "off" an enabled arrhythmia detection function. For example, a clinician may be interested only in monitoring ventricular arrhythmias, not atrial arrhythmias. The clinician may therefore program the enabled atrial arrhythmia detection functions to be "off". While an atrial arrhythmia detection function may be turned "off", it is enabled in terms of the device configuration and available to a user.

As such, "device configuration," as used herein, does not refer to the status of programmable (or non-programmable) operating parameters that are used to control the operation of enabled device functions. Rather, "device configuration" refers to the actual combination of device functions that are enabled and disabled, i.e., available or not available to a user. The device configuration will define which operating parameters will be displayed and available to the user for programming. While the user may choose to program the IMD 10 to not perform certain enabled functions at various times, those functions are enabled and available for use according to the device configuration.

As indicated above, the first device configuration may include device functions that are disabled. A user cannot program such device functions to be performed until the IMD 10 configuration is automatically updated by programmer 16 to a configuration that enables the disabled device functions in accordance with the stored update files 22. The IMD 10 is manufactured to include the capability of performing the disabled device functions, however the disabled device functions will not be executed as long as the IMD 10 remains in the first device configuration. Any disabled device functions and associated operating parameters will not be displayed by the programmer 16 as long as the IMD 10 remains in the first device configuration. Alternatively, disabled device functions may be displayed but indicated as being disabled.

The medical device system 8 may further include a networked remote patient management system 24 in communication with programmer 16 via communication link 26. Remote patient management system 24 may be used to retrieve data from programmer 16 or provide programmer 16 with IMD programming instructions, including update files 22 that are stored in programmer 16. Examples of remote patient management systems are described in U.S. Pat. No. 6,442,432 (Lee), hereby incorporated herein by reference in its entirety.

It is recognized that IMD 10 may include any number of leads or catheters (not shown) extending from IMD 10 for carrying electrodes, sensors or a fluid delivery lumen, for example, for use in performing IMD functions. Such leads may include subcutaneous leads, transvenous leads, and epicardial leads. Furthermore, IMD 10 may include any number of electrodes or sensors (not shown) incorporated on or in the housing of IMD 10. While the medical device system 8 shown in FIG. 1 includes an implantable medical device 10, embodiments of the present invention may alternatively include external medical devices, such as bedside devices or wearable, ambulatory, monitoring or therapy delivery devices.

Figure 2:
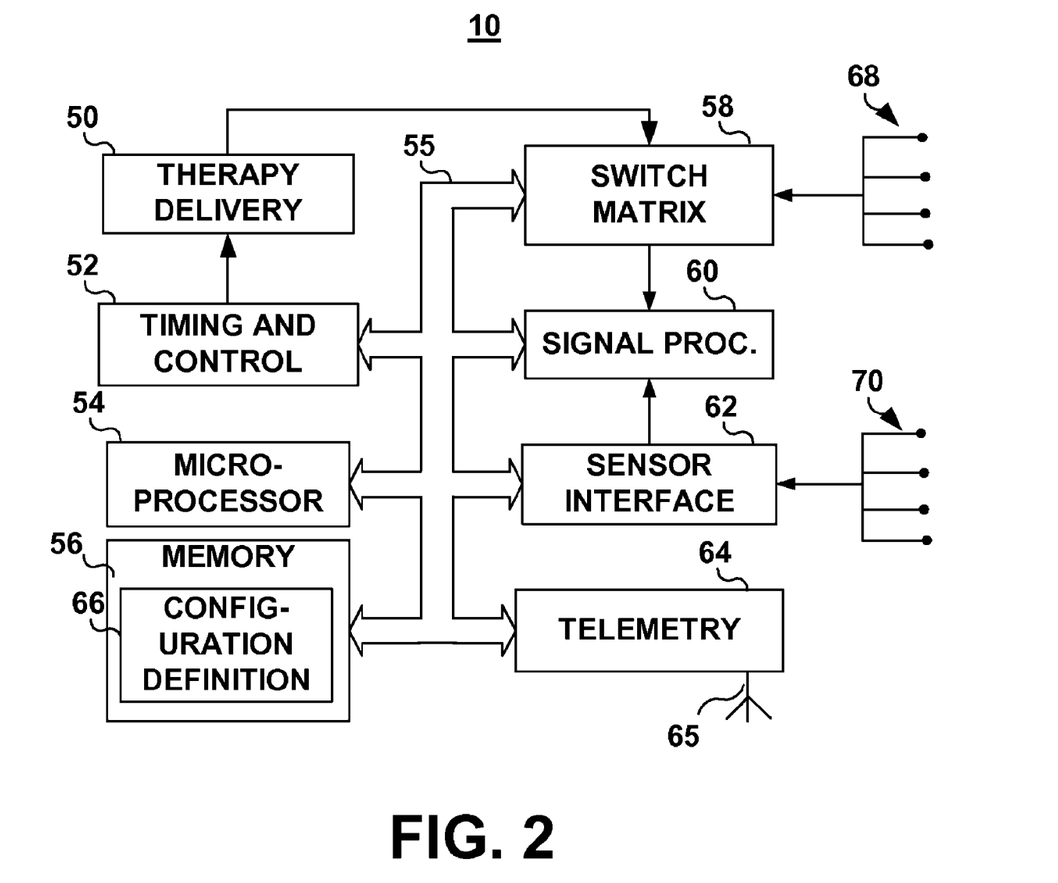
FIG. 2 is a functional block diagram of one embodiment of the implantable medical device shown in FIG. 1.

FIG. 2 is a functional block diagram of one embodiment of IMD 10 shown in FIG. 1. IMD 10 generally includes timing and control module 52 and an operating system that may employ microprocessor 54 for timing sensing and therapy delivery functions in accordance with a programmed operating mode. Microprocessor 54 and associated memory 56 are coupled to the various components of IMD 10 via a data/address bus 55. IMD 10 includes therapy delivery unit 50 for delivering patient therapies, such as electrical stimulation, drug delivery, or biological or genetic agents. Such therapies are delivered under the control of timing and control module 52. Electrical stimulation therapies may include cardiac pacing therapies and anti-arrhythmia therapies including cardioversion/defibrillation shocks. As such, therapy delivery unit 50 may be coupled to two or more electrode terminals 68 via a switch matrix 58. Switch matrix 58 is used for selecting which electrodes and corresponding polarities are used for delivering electrical stimulation pulses.

Electrode terminals 68 may be coupled to lead-based or leadless electrodes (incorporated in the IMD housing), and may be used for receiving electrical signals from the heart or other excitable body tissues for monitoring electrophysiological signals. Cardiac electrical signals are sensed for determining when an electrical stimulation therapy is needed and in controlling a stimulation mode and the timing of stimulation pulses.

Electrodes used for sensing and electrodes used for stimulation may be selected via switch matrix 58. When used for sensing, electrode terminals 68 are coupled to signal processing circuitry 60 via switch matrix 58. Signal processor 60 includes sense amplifiers and may include other signal conditioning circuitry and an analog to digital converter. Electrical signals may then be used by microprocessor 54 for detecting physiological events, such as detecting and discriminating cardiac arrhythmias.

IMD 10 may additionally or alternatively be coupled to one or more physiological sensors via physiological sensor terminals 70. Physiological sensors may include pressure sensors, accelerometers, flow sensors, blood chemistry sensors, activity sensors or other physiological sensors. Physiological sensors may be carried by leads extending from IMD 10 or incorporated in or on the IMD housing.

Signals received at sensor terminals 70 are received by a sensor interface 62 which provides sensor signals to signal processing circuitry 60. Sensor signals are used by microprocessor 54 for detecting physiological events or conditions. For example, IMD 10 may monitor impedance signals, heart wall motion, blood pressure, blood chemistry, respiration, or patient activity. Monitored signals may be used for sensing the need for delivering a therapy under control of the operating system.

The operating system includes associated memory 56 for storing a variety of programmed-in operating mode and parameter values that are used by microprocessor 54 in controlling device function. The memory 56 may also be used for storing data compiled from sensed physiological signals and/or relating to device operating history for telemetry out on receipt of a retrieval or interrogation instruction from a programmer. A device configuration definition 66, referred to hereafter as "configuration definition", is also stored in IMD memory 56. As will be further described herein, the configuration definition 66 stores data indicating the current IMD configuration and allowable device configurations. IMD memory 56 generally includes RAM and ROM memory, but may alternatively or additionally include EEPROM, NVRAM, flash memory or other memory structures.

IMD 10 further includes telemetry circuitry 64 and antenna 65. Programming commands or data are transmitted during uplink or downlink telemetry between IMD telemetry circuitry 64 and telemetry circuitry included in a programmer 16 (FIG. 1). Embodiments of the invention may be implemented in conjunction with any telemetry system or hardwired communication system. Examples of telemetry systems used in conjunction with implantable medical devices are disclosed in U.S. Pat. No. 5,354,319 (Wyborny et al.) and in U.S. Pat. No. 6,482,154 (Haubrich et al.), both of which patents are incorporated herein by reference in their entirety.

Figure 3:
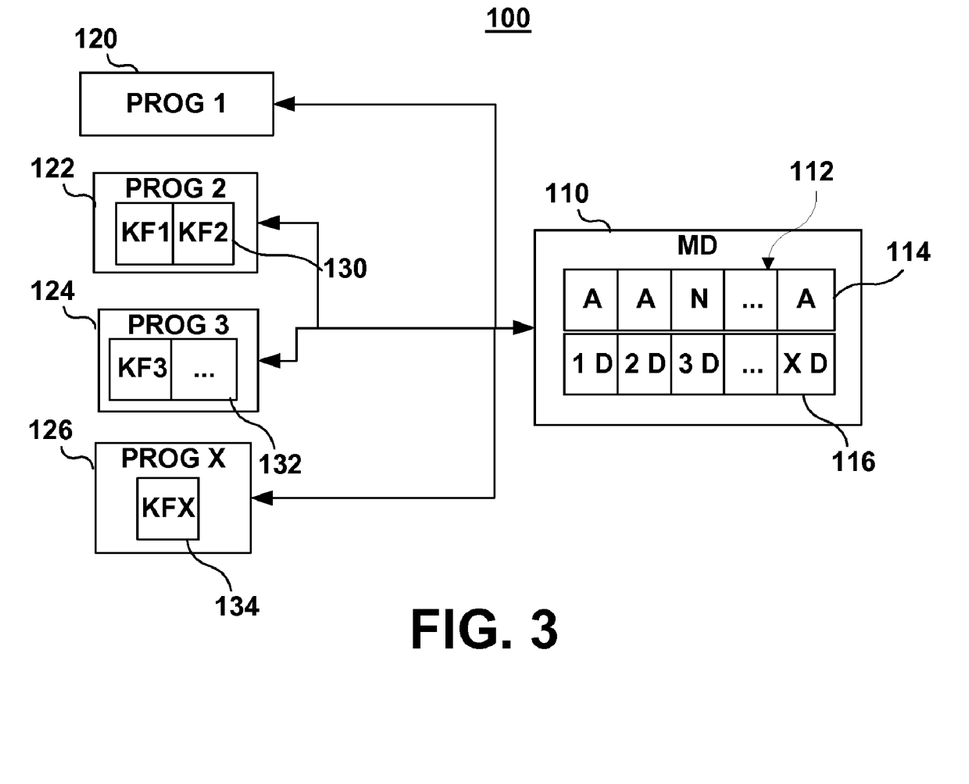
FIG. 3 is a schematic diagram of a medical system including a medical device configurable after device manufacture.

FIG. 3 is a schematic diagram of a medical system 100 including a medical device 110 having functionality that is configurable after device manufacture. Medical device (MD) 110 may be any implantable or external medical device and may correspond to IMD 10 shown in FIG. 2. MD 110 includes a configuration definition 112 stored in device memory. The configuration definition 112 includes at least two fields, an allowable status field 114 and a function status field 116 corresponding to each of several flexible device functions, 1 through "X".

Flexible device functions 1 through X may include any subset or all of the device functions that are implemented in MD 110. These device functions are "flexible" because they can be enabled or disabled after the time of device manufacture. Flexible device functions 1 through X may be functions that are still under clinical investigation at the time of device manufacture, awaiting approval by regulatory agencies, provided based on geographic distribution of MD 110, or enabled based on device pricing, patient indications, etc.

Such functions may include therapy delivery functions, such as pacing therapies, anti-arrhythmia therapies, drug therapies, or any other delivered therapy, as well as monitoring functions such as monitoring blood pressure, edema, blood chemistry, electrical signals, or any other physiological signals. Such functions may also include providing a particular device response to an existing device function and thus be dependent on another existing device function. For example, a flexible function may be to generate an alert signal or warning to the patient or a caregiver in response to detecting a physiological event. Flexible device functions may also include device diagnostic functions such as lead impedance tests, battery longevity analysis, memory checks or other functions performed to assess the device performance. Essentially any device function, whether it is dependent or independent of other device functions, can be implemented as a flexible device function.

For each flexible device function 1 through X, a bit included in the allowable status field 114 indicates whether updates to the corresponding device function are allowed (A) or not allowed (N). The allowable status field 114 is stored in firmware, ROM, EEPROM, NVRAM, or other non-volatile memory of MD 110. The allowable status field 114 is not programmable or changeable after device manufacture in one embodiment of the invention. As such, allowable status field 114 controls what device configurations are available in the particular MD 110. Even though a flexible device function is implemented in MD 110, enabling of that function may be permanently disallowed based on the allowable status field 114.

The function status field 116 includes multiple bits for each respective flexible device function 1 through X indicating the current status of the device function as being either disabled (D) or enabled (E). The function status field 116 is stored in RAM or other read-writable memory. The function status field 116 is automatically updated when the MD 110 encounters a programmer configured to update the device configuration of MD 110.

In a first device configuration, as shown in FIG. 3, flexible device functions 1 through X are all disabled as indicated by a "D" in the function status field 116. In other embodiments, a first device configuration may include flexible device functions that are enabled and/or disabled in any desired combination.

A number of programmer configurations 120, 122, 124, and 126 are associated with MD 110. The programmer configurations 120 through 126 may be successively implemented in a single programmer through software upgrades or may represent different programmers each having different states of software updates. Programmer configurations 120 through 126 may represent different programmers having different configurations based on the currently installed programmer software version. As used herein, the term "programmer configuration" refers to the current version of executable instructions, implemented in any combination of software and firmware, being executed by the programmer during communications with a medical device. Typically, a new programmer configuration is implemented by installing a new version of software in the programmer. The new software version may be installed by downloading the software from a centralized, networked computer, such as remote patient management system 24 (shown in FIG. 1), or using CD-ROM, or other computer-readable medium. Programmer configurations 120 through 126 may represent configurations that become available at different times, are distributed to different geographic areas, or are distributed to different clinics or hospitals according to clinical study plans.

A first programmer configuration (PROG 1) 120, can be used to interrogate and program MD 110. The first programmer configuration 120 does not include any programmer update files that cause a configuration update of MD 110. When first programmer configuration 120 is used to interrogate MD 110, the configuration definition 112 is read such that the first programmer configuration 120 is able to determine the current configuration of MD 110. If any of the device functions defined in the configuration definition 112 have been updated, i.e., enabled in this example, the first programmer configuration 120 will update the programmer display fields to appropriately display the enabled function and any associated programmable operating parameters, corresponding parameter value selections and related data. A display field for an updated device function may include the name of the function, physiological or device-related data stored by the IMD pertaining to the function and/or acquired as a result of performing of the enabled function, and programmable operating parameters that control operation of the function. As such, even though the first programmer configuration 120 is not configured to update the configuration definition 112, the first programmer configuration 120 is configured to read the configuration definition 112 and respond by generating appropriate programmer display fields for allowing display of enabled functions and inhibiting (or appropriately labeling) a display of disabled functions.

In some embodiments, programmer configuration 120 may be further configured to allow programming of enabled functions. A patient may be seen at a clinic having an updated programmer configuration that enables a flexible device function because the function has recently been approved by a regulatory agency. The patient may visit another clinic having the first programmer configuration 120. The first programmer configuration may be used to program the enabled device function.

In other embodiments, programmer configuration 120 may be configured to display enabled functions but may not allow programming of one or more enabled functions. In one scenario, a patient may be enrolled in a clinical study. The patient may be implanted with a medical device having a flexible device feature enabled for evaluation in the study. If that patient visits another clinic not participating in the study, a programmer in the non-participating clinic having programmer configuration 120 is able to read the configuration definition 112 and display the enabled function being evaluated. Programmer configuration 120 however may not be configured to program that function such that flexible device functions under clinical study cannot be altered by a non-participating clinic.

Programmer configuration 122 includes one or more update files 130, also referred to herein as "key files" (KF1 and KF2). The presence of update files 130 causes the programmer to execute software instructions to update the configuration definition 112 of MD 110. In this example, programmer configuration 122 includes two update files 130, KF1 and KF2, for updating flexible device functions 1 and 2, respectively. Upon interrogation of MD 110, programmer configuration 122 reads the configuration definition 112. Programmer configuration 122 identifies whether the flexible device functions defined in the configuration definition 112 correspond to functions (1 and 2) updatable using update files 130. If so, the programmer configuration 122 determines if the flexible device functions 1 and 2 have already been updated based on the function status field 116. If MD 110 has not previously been interrogated by programmer configuration 122, device functions 1 and 2 will still be disabled. If already enabled, programmer configuration 122 will respond by generating the appropriate display fields corresponding to device functions 1 and 2 and currently programmed settings.

If functions 1 and 2 have not been updated, programmer configuration 122 will check the allowable status field 114 to determine if updates to functions 1 and 2 are allowed. If allowed, the update files 130 are used to update the update status field 116. Update status field bits will be changed to indicate functions 1 and 2 are enabled. If the allowable status field 114 indicates updates to a corresponding device function are not allowed in MD 110, the corresponding function status field 116 is not updated by the programmer configuration 122 and the flexible device functions 1 and/or 2 will remain disabled. While the update file 130 is described here to enable previously disabled device functions, it is recognized that an update file may alternatively disable previously enabled device functions. Thus, "updating" may refer to either enabling or disabling a device function.

Other programmer configurations 124 and 126 may include additional update files 132 and 134 for updating additional device functions 3 through X. Whenever a programmer is used to interrogate MD 110, the configuration definition 112 is read. In response to reading the configuration definition 112, the programmer configuration 120, 122, 124 or 126 performs configuration updates in accordance with update files 130, 132 and 134 and as allowed by the allowable status field 112. The programmer additionally generates the appropriate programmer display fields corresponding to the current MD configuration as defined by the function status field 116. All of the programmer configurations 120 through 126 are able to display fields corresponding to MD functions that have been updated, regardless of which programmer configuration 120 through 126 actually performed the MD configuration update.

Figure 4:
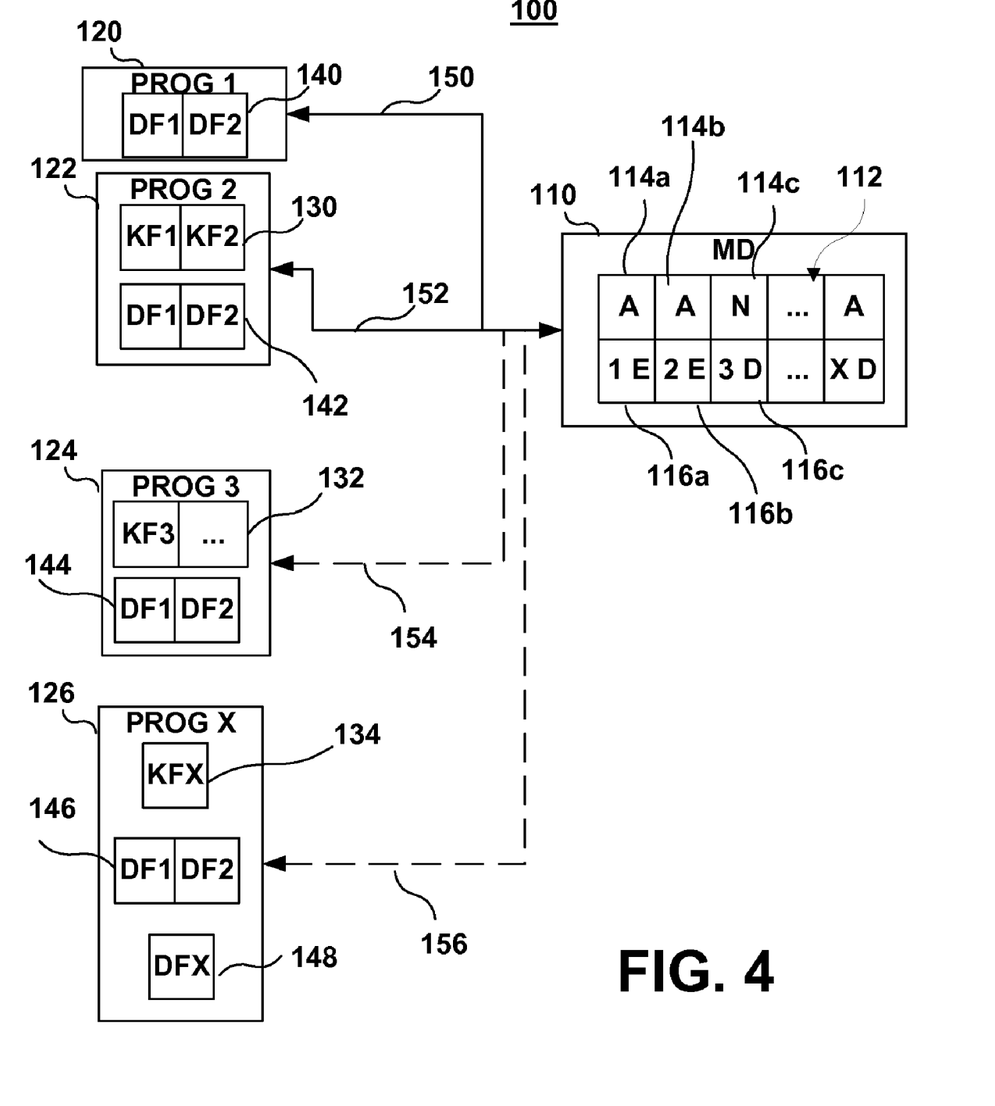
FIG. 4 is a schematic diagram of the medical device system shown in FIG. 3 after the medical device configuration has been updated.

FIG. 4 is a schematic diagram of the medical device system 100 shown in FIG. 3 after the device configuration of MD 110 has been updated. The allowable status field bits 114a and 114b for MD 110 allows device functions 1 and 2 to be updated by programmer configuration 122 as generally described above. Device function 3 is not allowed to be updated as defined by bit 114c in allowable status field 114 of configuration definition 112. In FIG. 4, MD 110 has been updated to a second device configuration in response to being interrogated by programmer configuration 122 using communication link 152. Programmer configuration 122 includes update files 130 for enabling device function 1 and device function 2. Function status field bits 116a and 116b have been updated, as indicated by an "E", to indicate that functions 1 and 2 are now enabled.

After being updated to the second device configuration, any of the programmer configurations 120 through 126 can be used to interrogate MD 110 using respective communication links 150, 152, 154, and 156. In response to interrogating MD 110 and reading the second device configuration as defined by the updated configuration definition 112, programmer configurations 120 through 126 will generate display field 1 (DF1) and display field 2 (DF2) in displays 140, 142, 144, and 146, respectively. DF1 and DF2 correspond to the enabled device functions 1 and 2 and include any programmable operating parameters along with selectable parameter values and/or associated data corresponding to the enabled device functions 1 and 2.

The configuration definition 112 does not allow a third device function to be enabled as indicated by the "N" in allowable status field bit 114c. If programmer configuration 124 is used to interrogate MD 110, the configuration definition 112 will be read and device function "3" will remain disabled, as indicated by the "D" in update status field bit 116c even though programmer configuration 124 includes an update file (KF3) 132 for enabling the device function 3.

At a future point in time, if programmer configuration 126 is used to interrogate MD 110, device function X will be updated in response to programmer update file (KFX) 134 and the allowable status bit in allowable status field 112 indicating function X is updatable. A display field 148 will be generated in association with the enabled device function X. After function X is updated, programmer configurations 120 through 124 will also generate a display field corresponding to function X upon interrogating MD 110 and reading configuration definition 112.

As indicated previously, programmer update files may include files for enabling or disabling device functions. One programmer configuration may include update files that cause enabling of a device function and another programmer configuration may include update files that cause disabling of the same device function. For example, if a patient enrolled in a clinical study exits the study, a programmer configuration for disabling the device function under evaluation may be used to disable that device function.

Figure 5:
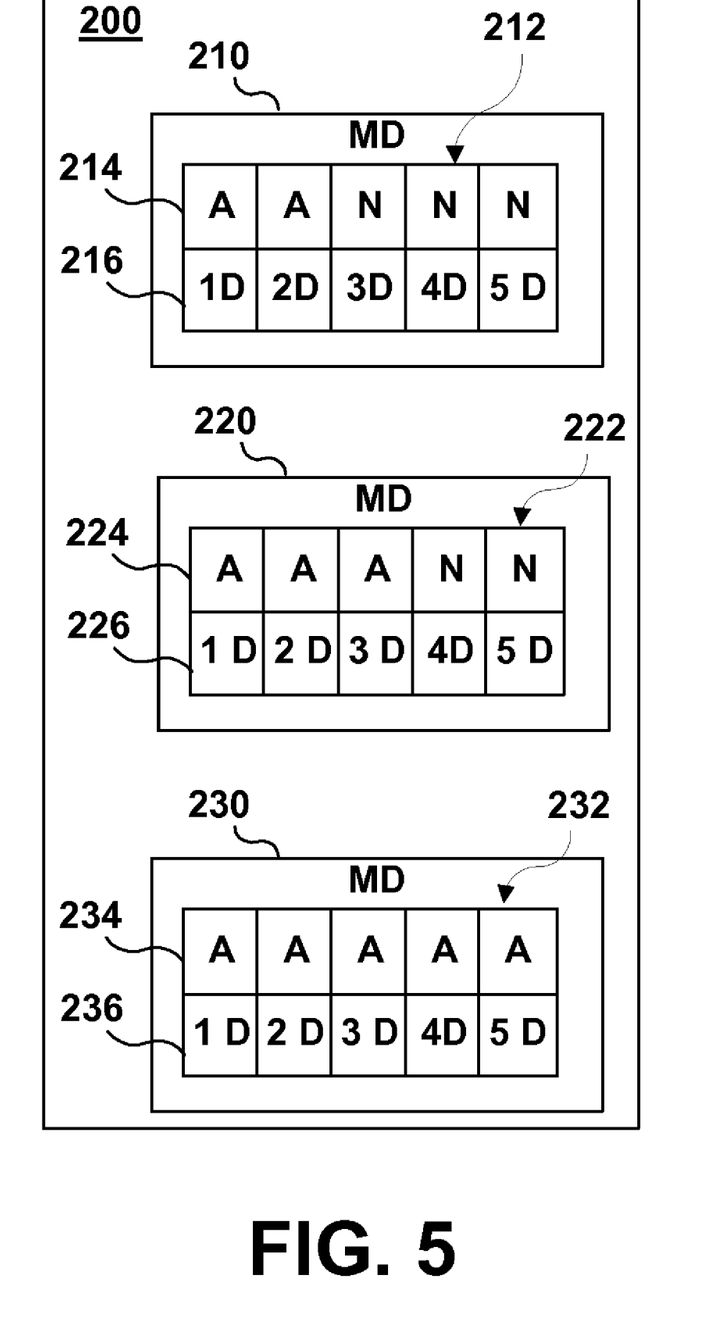
FIG. 5 is a diagram of different levels of configuration definitions that may be included in medical devices.

FIG. 5 is a diagram of different levels of configuration definitions that may be included in medical devices. A large number of medical devices may be manufactured and provided with the same initial device configuration but sold at different prices, in different geographic areas, or distributed to different clinical centers. As such, it may be desirable to provide the medical devices with different device configurations. Furthermore, it may be desirable to control which device configurations can be enabled in which devices, e.g. based on pricing or distribution of the devices and according to a particular model number. The allowable status field in the configuration definition provides such control over the medical device configurations. Even though all of the devices may be manufactured with the same initial device configuration and include the same set of flexible functions, the configuration updates possible after device manufacture are controlled by the allowable status field.

Accordingly, different batches or models of devices may be provided allowing varying levels or hierarchies of device configurations. Out of a large number of manufactured devices all having the same first device configuration, different batches or models of those devices may be provided with different configuration definitions indicating different allowed or disallowed device function updates. Some device models may be provided with a configuration definition allowing no flexible functions to be enabled; other device models may be provided with a configuration definition allowing all flexible functions to be enabled, and still other device models may be provided with configuration definitions allowing different subsets of the flexible device functions to be enabled. All of these various models, however, may be manufactured with identical device configurations initially.

In FIG. 5, a lot 200 of medical devices is manufactured. The devices in lot 200 are divided into three batches or models 210, 220 and 230. Each device in batches or models 210, 220, and 230 is provided with a configuration definition 212, 222, and 232, respectively. All three models 210, 220 and 230 of devices share the same first device configuration as defined by the function status fields 216, 226 and 236 of configuration definitions 212, 222, and 232. In this example, the first device configuration is defined by five flexible device functions, 1 through 5, all being disabled.

Each model 210, 220 and 230, however, is provided with a unique allowable status field 214, 224, and 234, respectively. In model 210, allowable status field 214 includes bits indicating only flexible device functions 1 and 2 are updatable as indicated by an "A". Flexible device functions 3, 4 and 5 are not updatable as indicated by an "N" in allowable status field 214.

In model 220, allowable status field 224 indicates updates to flexible device functions 1, 2 and 3 are allowable (A). Updates to flexible device functions 4 and 5 are not allowed (N). In model 230, all five of the flexible device functions 1 through 5 are updatable according to the allowable status indicator field 234.

By defining three different allowable status fields 214, 224, and 234 for the three different device models 210, 220 and 230, respectively, devices 200 may be distributed, for example, at different prices, in different geographic regions, according to different patient indications, etc., based on the available device configurations as defined by the allowable status fields 214, 224, and 234.

Figure 6:
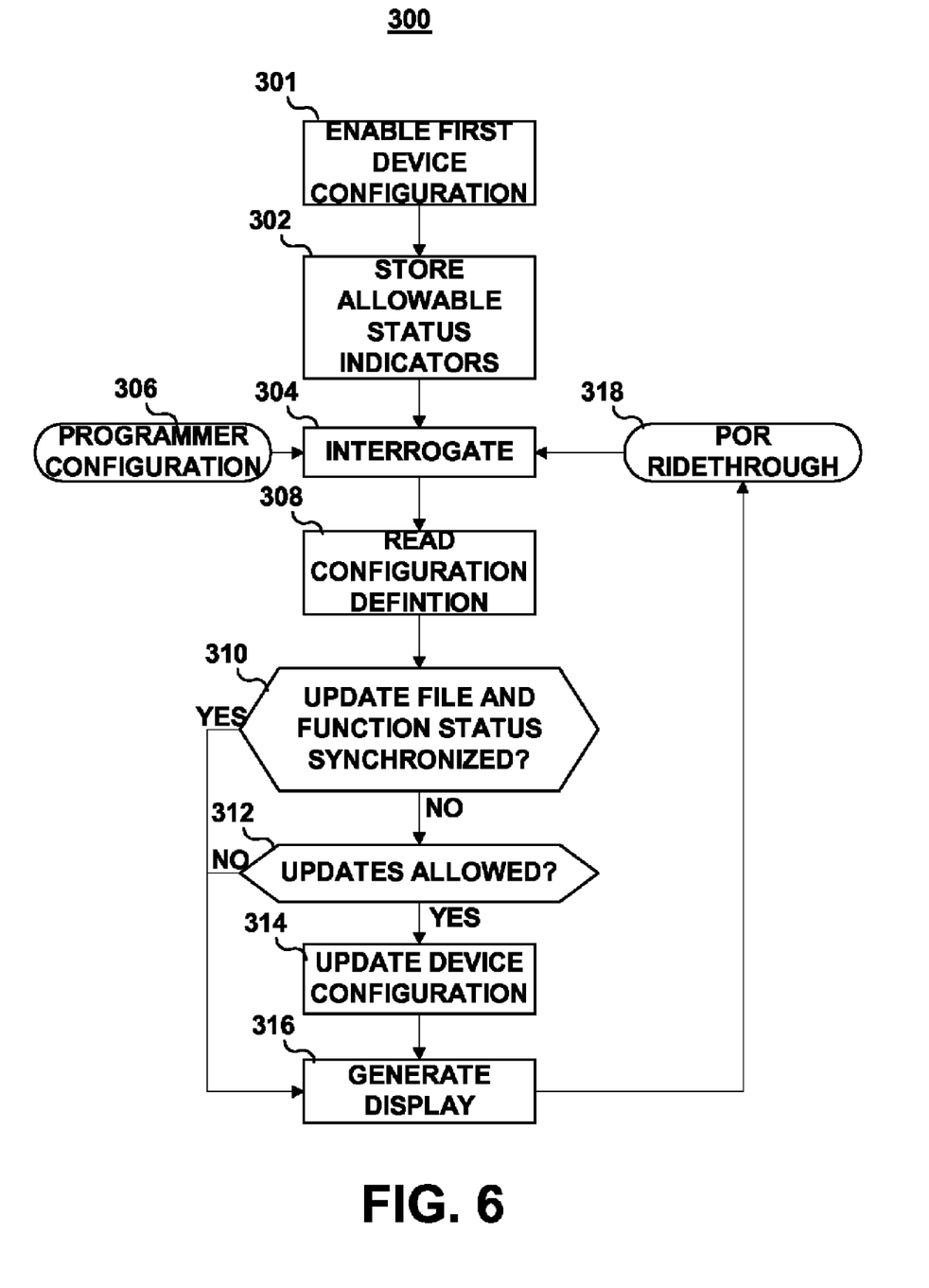
FIG. 6 is a flow chart of a method for updating a device configuration in a medical device according to an embodiment of the present invention.

FIG. 6 is a flow chart of one method for updating a device configuration in a medical device according to an embodiment of the present invention. Flow chart 300 is intended to illustrate the functional operation of a medical device system for configuring a medical device and should not be construed as reflective of a specific form of software or hardware necessary to practice the invention. It is believed that the particular form of software will be determined primarily by the particular system architecture employed in the medical device and by the programmer. Providing software to accomplish the present invention in the context of any modern medical device system, given the disclosure herein, is within the abilities of one of skill in the art.

At block 301, a first device configuration is enabled at the time of device manufacture. The first device configuration is defined according to a number of function status field bits indicating the status, i.e., enabled or disabled, of a corresponding number of flexible device functions. At block 302, allowable status indicators are stored for each of the flexible device functions implemented in the medical device. At block 304, the medical device is interrogated by a programmer having a programmer configuration 306. The programmer configuration reads the configuration definition stored in the medical device at block 308.

The configuration definition read at block 308 includes both a function status field and an allowable status field, each including at least one indicator bit for each of the flexible device functions. At block 310, the function status field is compared to any available update files included in the programmer configuration 306 used to interrogate the medical device. If the function status for each flexible device function corresponding to the programmer update files indicates that the function has already been updated, i.e. the update files and function status field are synchronized, no updating of the device configuration is performed.

The programmer generates an appropriate display at block 316 based on the read configuration definition. Any flexible device functions that are enabled, in response to the current programmer configuration, or previously enabled by another programmer configuration, are displayed along with any available programmable operating parameters.

If the update files included in the interrogating programmer configuration and the function status of the flexible device functions are not synchronized (i.e. the flexible functions have not been updated in accordance with the programmer update files), the programmer determines if updates to the corresponding device functions are allowed as defined by the allowable status field. If not allowed, the device configuration remains unchanged and the appropriate programmer display is generated at block 316. If updates of the flexible device functions corresponding to the programmer update files are allowed, the device configuration is updated at block 314 under the control of the update files. The appropriate programmer display fields are then generated at block 316.

At any time during device operation, a power-on reset may occur at block 318 due to varying levels of triggering events. If a device reset occurs, the current function status field may be retained in the device memory, such as in RAM, so that the device configuration will be retained when the device is interrogated by any programmer configuration, with or without update files.

Thus, a system and method for configuring a medical device have been presented in the foregoing description with reference to specific embodiments. It is appreciated that various modifications to the referenced embodiments may be made without departing from the scope of the invention as set forth in the following claims.

The invention claimed is:
1. A method for configuring a medical device, comprising:
setting a first device configuration of the medical device corresponding to a configuration definition stored in a memory of the medical device comprising both one allowable status field bit and one function status field bit corresponding to each of a plurality of medical device functions, the function status field bit indicating a current status of a respective medical device function as being enabled or disabled and the allowable status field bit indicating whether updates to the function status field bit of the respective medical device function are allowed or not allowed;
interrogating the medical device using a first programmer configuration configured to update the first device configuration;

automatically comparing the first programmer configuration and the first device configuration in response to the interrogating; and automatically setting a second device configuration of the medical device by updating the function status field bit for at least one of the plurality of medical device functions in response to the comparison of the first programmer configuration and the first device configuration if the allowable status field bit for the at least one of the plurality of medical device functions indicates updates to the respective function status field bit are allowed, wherein the updating comprises switching between an enabled and a disabled status.

2. The method of claim 1 further comprising updating a programmer display field in response to setting the second device configuration.

3. The method of claim 1 further comprising:
interrogating the medical device using a second programmer configuration not configured to update the first device configuration, and
updating a programmer display field in response to the second device configuration.

4. The method of claim 3 wherein the second programmer configuration is further configured to allow operating parameters corresponding to the at least one of the plurality of medical device functions to be programmed in response to the function status field bit for the at least one of the plurality of medical device functions being enabled in the second device configuration.

5. The method of claim 1, further comprising:
interrogating the medical device using a second programmer configuration configured to update the second medical device configuration;
automatically comparing the second programmer configuration and the second device configuration in response to the interrogating;
automatically setting a third device configuration of the medical device by updating the function status field bit for at least one of the plurality of medical device functions in response to the allowable status field bit for the at least one of the plurality of medical device functions.

6. The method of claim 1, wherein the allowable status field bit for each of the plurality of medical device functions is fixed at a time of medical device manufacture and is not updatable.

7. The method of claim 1 wherein the first programmer configuration comprises an update file for updating the first device configuration.

8. A medical device system, comprising:
a programmable medical device comprising a memory and a configuration definition stored in the memory, the configuration definition comprising both one allowable status field bit and one function status field bit corresponding to each of a plurality of medical device functions, the function status field bit indicating a current status of a respective medical device function as being enabled or disabled and the allowable status field bit indicating whether updates to the function status field bit of the respective medical device function are allowed or not allowed;
a first programmer configuration configured to update the configuration definition wherein updating the configuration definition comprises automatically comparing the first programmer configuration and the configuration definition in response to interrogating the medical device using the first programmer configuration and automatically setting an updated configuration definition by updating the function status field bit for at least one of the plurality of medical device functions in response to the comparing of the first programmer configuration and the configuration definition if the allowable status field bit for the at least one of the plurality of medical device functions indicates updates to the respective function status field bit are allowable, wherein the updating comprises switching between an enabled and a disabled status.

9. The system of claim 8 wherein the first programmer configuration comprises a display and wherein the programmer configuration is further configured to update a programmer display field in response to updating the configuration definition.

10. The system of claim 8 further comprising:
a second programmer configuration not configured to update the configuration definition,
the second programmer configuration comprising a display and being configured to update a display field in response to the updated configuration definition.

11. The system of claim 10 wherein the second programmer configuration is further configured to allow operating parameters corresponding to the at least one of the plurality of medical device functions to be programmed in response to the function status field bit for the at least one of the plurality of medical device functions being enabled in the updated configuration definition.

12. The system of claim 10, wherein updating a display field comprises one of inhibiting a display of a disabled function and labeling a display of a disabled function in response to the updated configuration definition comprising a function status field bit corresponding to a disabled status.

13. The system of claim 8 further comprising a second programmer configuration configured to update the updated configuration definition by updating the function status field bit for at least one of the plurality of medical device functions in response to the allowable status field bit for the at least one of the plurality of medical device functions.

14. The system of claim 8 wherein the allowable status field bit for each of the plurality of medical device functions is fixed at a time of medical device manufacture and is not updatable.

15. The system of claim 8 wherein the first programmer configuration comprises an update file for updating the first device configuration.

16. A non-transitory computer-readable medium for storing a set of instructions which when implemented in a medical device system cause the system to:
set a first device configuration of a medical device corresponding to a configuration definition stored in a device memory and comprising both one allowable status field bit and one function status field bit corresponding to each of a plurality of medical device functions, the function status field bit indicating a current status of a respective medical device function as being enabled or disabled and the allowable status field bit indicating whether updates to the function status field bit of the respective medical device function are allowed or not allowed;
automatically compare a first programmer configuration and the first device configuration in response to interrogating the medical device using the first programmer configuration; and
automatically set a second device configuration of the medical device by updating the function status field bit for at least one of the plurality of medical device functions in response to comparing of the first programmer configuration and the first device configuration if the allowable status field bit for the at least one of the plurality of medical device functions indicates updates to the function status field bit are allowed, wherein the updating comprises switching between an enabled and a disabled status.

17. An implantable medical device, comprising:

a memory;

a device configuration definition stored in the memory, the device configuration definition comprising both one allowable status field bit and one function status field bit corresponding to each of a plurality of medical device functions, the function status field bit indicating a current status of a respective medical device function as being enabled or disabled and the allowable status field bit indicating whether updates to the function status field bit of the respective medical device function are allowed or not allowed;

telemetry circuitry for establishing a communication link with a programmer and for receiving an update instruction for updating the device configuration definition; and a processor for updating the function status field bit for at least one of the plurality of medical device functions in response to the allowable status field bit for the at least one of the plurality of medical device functions indicating updates to the function status field bit are allowed and the update instruction, wherein the updating comprises switching between an enabled and a disabled status.

18. The implantable medical device of claim 17 wherein the allowable status field bit for each of the plurality of medical device functions is fixed at a time of implantable medical device manufacture and is not updatable.

19. A medical device system, comprising:

a plurality of programmable medical devices each comprising a memory and a device configuration definition stored in the memory, the configuration definition comprising both one allowable status field bit and one function status field bit corresponding to each of the plurality of medical device functions, the function status field bit indicating a current status of a respective medical device function as being enabled or disabled and the allowable status field bit indicating whether updates to the function status field bit of the respective medical device function are allowed or not allowed;

a programmer comprising a memory and an update file stored in the memory for updating the configuration definition wherein updating the configuration definition comprises automatically comparing the update file and the configuration definition in response to interrogating one of the plurality of the medical devices using the programmer and automatically updating the configuration definition of the one of the plurality of medical devices by updating the function status field bit for at least one of the plurality of medical device functions in response to the comparing of the update file and the configuration definition if the allowable status field bit indicates updates to the function status field bit are allowed for the at least one of the plurality of medical device functions, wherein the updating comprises switching between an enabled and a disabled status;

wherein the plurality of programmable medical devices comprises a first set of devices having a first configuration definition comprising a first allowable status field and a second set of devices having a second configuration definition wherein the second configuration definition includes a second allowable status field defined uniquely different than the first allowable status field.

* * * * *